United States Patent [19]

Neumann et al.

[11] Patent Number: 5,079,149
[45] Date of Patent: Jan. 7, 1992

[54] PROCESS FOR THE PREPARATION OF PURPLE MEMBRANE CONTAINING BACTERIORHODOPSIN

[75] Inventors: Stefan Neumann, Kastl; Horst Leigeber, Oberhaching, both of Fed. Rep. of Germany

[73] Assignee: Industrie GmbH, Munich, Fed. Rep. of Germany

[21] Appl. No.: 510,605

[22] Filed: Apr. 17, 1990

[30] Foreign Application Priority Data

Jul. 5, 1989 [DE] Fed. Rep. of Germany ....... 3922133

[51] Int. Cl.$^5$ .................. C07K 3/20; C07K 15/22
[52] U.S. Cl. .................. 435/712; 435/711; 530/412; 530/417; 530/802; 530/825; 530/400
[58] Field of Search ............ 530/412, 417, 802, 825, 530/400; 435/71.1, 71.2

[56] References Cited

PUBLICATIONS

Schegle et al., EMBO J. vol. 7(9), pp. 2925-34 (1988).
Seignevret et al., FEBS Lett. vol. 228 (1) pp. 79-84 (1988).
Hegemann et al. EMBO J. vol. 1 (10) pp. 1177-84 (1982).
Huang et al., Proc. Natl. Acad. Sci. U.S.A. vol. 77 (1), pp. 323-7 (1980).
Happe et al., Biochem. Biophys. Res. Comm. vol 72 (4) pp. 1504-11 (1976).
Biosystems 1986,19, 223-236, The Bacteriorhodopsin Model Membrane System as a Prototype Molecular Computing Element, F. T. Hong.
Biophysics 1985, 30 (5), 962-967, Biological Light-Sensitive Complexes as Technical Information Photocarriers, N. N. Vsevolodov, G. R. Ivanitskii.
Nature 1971, 233, 149-154, Rhodopsin-like Protein from the Purple Membrane of Halobacterium Halobium D. Oesterhelt, W. Stoeckenius.
Methods in Enzymology 1974, 31, 667-678, Isolation of the Cell Membrane of Halobact. Halobium and its Fractionation into Red and Purple Membrane, D. Oesterhelt, W. Stoeckenius.
Preparative Biochemistry 1975, 5 (2), 161-178, Improved Isolation Procedures for the Purple Membrane of Halobacterium Halobium. B. M. Becher, J. Y. Cassim.

*Primary Examiner*—F. T. Moezie
*Assistant Examiner*—Andrew G. Rozycki
*Attorney, Agent, or Firm*—Collard, Roe & Galgano

[57] ABSTRACT

The invention relates to a process for the preparation of purple membrane containing bacteriorhodopsin, which process comprises obtaining, in a manner know per se, the cell membrane from halobacteria cells, and subjecting the material to gel filtration chromatography in order to isolate the purple membrane from the cell membrane.

6 Claims, No Drawings

PROCESS FOR THE PREPARATION OF PURPLE MEMBRANE CONTAINING BACTERIORHODOPSIN

BACKGROUND OF THE INVENTION

1. Field of the Invention

The invention relates to a process for the preparation of purple membrane containing bacteriorhodopsin.

2. The Prior Art

Bacteriorhodopsin is a chromoprotein which is formed by halobacteria, such as *Halobacterium halobium*. It consists of a protein moiety (bacterioopsin) and a chromophore (retinal), and it occurs in the cell membrane of halobacteria in the form of the so-called purple membrane (hereinafter also called PM). In the PM, bacteriorhodopsin is arranged in a two-dimensional crystalline, hexagonal lattice. By virtue of its physical properties, bacteriorhodopsin might be employed in biocomputers (cf. Biosystems 1986, 19, 223-236) or as a holographic storage material in optical data processing (cf. Biophysics 1985, 30(5), 962-967). For this purpose, however, it is necessary to be able to obtain large amounts of purple membranes. Since the physical differences between purple membranes and contaminating membrane fragments which do not contain bacteriorhodopsin are small, it is difficult to separate the purple membrane from the contaminating fragments.

According to D. Oesterhelt, W. Stoeckenius, Nature 1971, 233, 149-154, and Methods in Enzymology 1974, 31, 667-678, it is known to carry out the preparation by centrifugation of the purple membrane in a sucrose density gradient from 0.5 to 1.5M or from 30 to 50% by weight sucrose. B. M. Becher, J. Y. Cassim, Preparative Biochemistry 1975, 5(2), 161-178, describe a centrifugation of the purple membrane by means of a stepped sucrose gradient having steps of 45, 40, 38, 36 and 16% by weight of sucrose.

Due to the complicated apparatus in these gradient centrifugations, which, for example, require ultracentrifuges, a variable scale-up with regard to the amounts of bacteriorhodopsin to be obtained is not possible, which means that only comparatively low amounts of PM are isolated in one work-up.

Furthermore, the preparation of the sucrose gradients and the removal of the employed sucrose from the PM obtained are procedure steps which involve large amounts of time.

SUMMARY OF THE INVENTION

The invention relates to a process for the preparation of purple membrane containing bacteriorhodopsin from halobacteria cells having a cell membrane comprising:
a) obtaining cell material including the cell membrane from halobacteria cells, and
b) subjecting the cell material to gel filtration chromatography in order to isolate the purple membrane from the cell membrane.

To prepare the cell membrane, halobacteria such as *Halobacterium halobium* are cultured in a manner known per se under conditions which favor the formation of purple membranes, such as, for example, low oxygen content of the medium and light (see D. Oesterhelt, W. Stoeckenius, Methods in Enzymology 1974, 31, 667-678). After the appropriate culture period, the cells are harvested, for example by centrifugation. The cell membrane is obtained from the resulting biomass in a manner known per se. It is preferred to carry out a dialysis against deionized water, followed by collection of the cell membrane by centrifugation. This membrane fraction, which contains the purple membrane, is subsequently washed, preferably using deionized water.

In the process according to the invention, these cell membrane fractions are applied to a chromatography column packed with a gel filtration material or packing which has an exclusion range with respect to molecular weight of preferably $2 \times 10^6$ to $10^9$, and more preferably $10^7$–$10^9$, and the column is eluted at a temperature of preferably 1° to 30° C., and more preferably 4° to 10° C., preferably using water having a preferred specific conductivity of preferably 0.05 to 5 $\mu$S/cm, and more preferably 0.1 to 1.0 $\mu$S/cm, and a pH of preferably 6.0 to 7.5, and more preferably of 6.3–6.7.

The chromatography column can have any desired length or diameter, the amount of cell membrane to be purified being decisive. For example, columns having a length of 50 to 100 cm and a diameter of 1.5 to 5 cm have proven advantageous for amounts of 10 to 100 mg of cell membrane.

The amount of the separation material used is preferably 5-15 ml per mg of cell membrane to be purified, and more preferably of 9 to 11 ml/mg.

The elution rate is preferably 0.25 to 16 cm/h, and more preferably of 0.5 to 6 cm/h. The process preferably is carried out in a pressure range of 0-5 bar superatmospheric pressure, and more preferably of 0-500 mbar superatmospheric pressure.

It is preferred to employ gel filtration materials of a particle size of 20-150 $\mu$m, and more preferably of 40-105 $\mu$m.

The gel filtration materials or packing employed according to the invention are those which have also been used hitherto in gel filtration. It is preferred to use crosslinked or non-crosslinked dextrans, agarose derivatives or copolymers of oligoethylene glycol, glycidyl methacrylate and pentaerythrol dimethacrylate.

Particularly preferred gel filtration materials are SEPHACRYL S 1000 (a registered trademark of Pharmacia AB, Uppsala, Sweden), BIOGEL A 150 m (a registered trademark of BioRad Laboratories, Richmond, Calif. U.S.A.) and FRACTOGEL TSK HW 75 (a registered trademark of Merck, Darmstadt, FRG).

The invention will now be described in further detail with reference being made to the following examples. It should, however, be recognized that the examples are given as being illustrative of the present invention and are not intended to define the spirit and scope thereof.

EXAMPLE 1

COMPARISON EXAMPLE 13 g of cell paste of *Halobacterium halobium* were resuspended in 90 ml of a solution of 250 g/l of NaCl, 20 g/l of $MgSO_4.7H_2O$, 3 g/l of trisodium citrate and 2 g/l of KCl, and the solution was treated with 5 mg of deoxyribonuclease and stirred for one hour. The cell suspension was subsequently dialyzed for 16 hours against deionized water. The dialyzate was centrifuged for 10 minutes at 7,600 g, and the supernatant was centrifuged for 30 minutes at 38,000 g to prepare the membranes. The resulting membrane sediment was washed with 80 ml of water having a specific conductivity of 0.1 $\mu$S/cm, and the material was recentrifuged at 38,000 g. The precipitate which contained 20 mg of PM was taken up in 3 ml of deionized water, and the sample was applied to a total of 5 sucrose density gradients having a sucrose content of 30-50% (w/w), each having a volume of 28 ml. The density gradients were subsequently centrifuged for 16 hours in an ultracentrifuge at 100,000 g. The density gradients were then fractionated, and the PM-containing fractions were combined and diluted with twice the volume of deionized water. The dilute PM suspension was then centrifuged for 30 minutes at 38,000 g, and the resulting PMs were washed once more with 100 ml of deionized water and recentrifuged for 30 minutes at 38,000 g. The precipitate obtained in this step was taken up in a little deionized water. 14 mg of PM were obtained.

EXAMPLE 2

35 g of cell paste of *Halobacterium halobium* were resuspended in 270 ml of a solution of 250 g/l of NaCl, 20 g/l of $MgSO_4.7H_2O$, 3 g/l of trisodium citrate and 2 g/l of KCl, and the suspension was treated with 15 mg of deoxyribonuclease and stirred for one hour. The cell suspension was subsequently dialyzed for 16 hours against deionized water. The dialyzate was centrifuged for 10 minutes at 7,600 g, and the supernatant was centrifuged for 30 minutes at 38,000 g to prepare the membranes. The resulting membrane sediment was washed with 240 ml of water having a specific conductivity of 0.1 $\mu$S/cm and pH 6.7, and the material was recentrifuged at 38,000 g. The precipitate which contained 80 mg of PM was then taken up in 7 ml of water of the above purity and pH, and the batch was applied to a column of a length of 75 cm and a diameter of 5.0 cm, which had been packed with SEPHACRYL S 1000 and equilibrated with water having a specific conductivity of 0.1 $\mu$S/cm and a pH of 6.7. Elution was effected at 5° C. at an elution rate of 2 cm per hour. The PM-containing fractions were combined, and the PMs were obtained by centrifugation for 30 minutes at 38,000 g. 60 mg of purple membrane were obtained. The optical spectrum of these membranes agreed with that of bacteriorhodopsin, and no impurities were found.

EXAMPLE 3

The procedure utilized was analogous to that of Example 2, with the difference that the elution rate during column chromatography was 5.7 ml per hour. 72 mg of purple membrane were obtained, which corresponds to a yield of 90% in the column chromatography.

EXAMPLE 4

14 g of cell paste of *Halobacterium halobium* were resuspended in 90 ml of a solution of 250 g/l of NaCl, 20 g/l of $MgSO_4.7H_2O$, 3 g/l of trisodium citrate and 2 g/l of KCl, and the suspension was treated with 5 mg of deoxyribonuclease and stirred for one hour. The cell suspension was subsequently dialyzed for 16 hours against deionized water. The dialyzate was centrifuged for 10 minutes at 7,600 g, and the supernatant was centrifuged for 30 minutes at 38,000 g to prepare the membranes. The resulting membrane sediment was washed with 80 ml of water having a specific conductivity of 0.1 $\mu$S/cm, and recentrifuged at 38,000 g. The precipitate which contained 20 mg of PM was then taken up in 2.5 ml of water of the above purity and pH, and the batch was applied to a column having a length of 60 cm and a diameter of 2.5 cm which had been packed with SEPHACRYL S 1000 and equilibrated with water having a specific conductivity of 0.1 $\mu$S/cm and a pH of 6.6. Elution was effected at 5° C. at an elution rate of 4.6 cm per hour. The PM-containing fractions were combined, and the PMs were obtained by centrifugation for 30 minutes at 38,000 g. 15 mg of purple membrane were obtained. The optical spectrum of these membranes agreed with that of bacteriorhodopsin, and no impurities were found.

EXAMPLE 5

The procedure utilized was analogous to that of Example 4, with the difference that the chromatography was carried out at 10° C. 18 mg of purple membranes were obtained, which corresponds to a yield of 80% in the column chromatography.

EXAMPLE 6

The procedure utilized was analogous to that of Example 4, with the difference that the specific conductivity of the water was 0.8 $\mu$S/cm and the pH was 6.5. 16 mg of PM were obtained, which corresponds to a yield of 82% in the column chromatography.

EXAMPLE 7

The procedure utilized was analogous to that of Example 4, with the difference that the chromatography step was carried out using a column having a length of 80 cm and a diameter of 2.5 cm, which had been packed with SEPHACRYL S 1000. 15 mg of purple membrane were obtained, which corresponds to a yield of 85% in the column chromatography.

EXAMPLE 8

The procedure utilized was analogous to that of Example 4, with the difference that TSK HW 75, made by Merck, Darmstadt, FRG, was used as the separating material. 17 mg of purple membrane were obtained. The yield in the column chromatography was 60%.

EXAMPLE 9

The procedure utilized was analogous to that of Example 4, with the difference that a 50 $\mu$molar phosphate buffer of pH 6.5 was used as the eluent. 18 mg of purple membrane were obtained. In this Example, the yield was 85%.

While only several embodiments and examples of the present invention have been shown and described, it will be obvious to those skilled in the art that many modifications may be made to the invention without departing from the spirit and scope thereof.

What is claimed is:

1. A process for the preparation of purple membrane containing bacteriorhodopsin from halobacteria cells having a cell membrane consisting essentially of:
   (a) obtaining cell material including the cell membrane from halobacteria cells; and
   (b) subjecting the cell material to gel filtration chromatography in order to isolate the purple membrane from the cell membrane.

2. The process as claimed in claim 1, employing an eluent having a specific conductivity of 0.05-5 $\mu$S/cm.

3. The process as claimed in claim 2, wherein water is employed as the eluent.

4. The process as defined in claim 3, wherein said eluent has a pH of 6.0 to 7.5.

5. The process as claimed in claim 1, effecting the chromatography at a temperature of 1° C. to 30° C.

6. The process as claimed in claim 1, wherein gel filtration packing has an exclusion range of $2 \times 10^6$ to $10^9$ Daltons.

* * * * *

UNITED STATES PATENT AND TRADEMARK OFFICE
CERTIFICATE OF CORRECTION

PATENT NO. : 5,079,149
DATED : January 7, 1992
INVENTOR(S) : Stefan NEUMANN and Horst LEIGEBER It is certified that error appears in the above-identified patent and that said Letters Patent is hereby corrected as shown below:

Cover page, column 1, item 73, before "Industrie" insert --Consortium fur elektrochemische--.

Signed and Sealed this

Eighth Day of June, 1993

Attest:

MICHAEL K. KIRK

Attesting Officer     Acting Commissioner of Patents and Trademarks